US005840213A

United States Patent [19]

Mazac et al.

[11] Patent Number: 5,840,213
[45] Date of Patent: *Nov. 24, 1998

[54] USES OF HEPTAFLUOROPROPANE

[75] Inventors: Charles J. Mazac; John S. Rubacha, both of West Lafayette, Ind.

[73] Assignee: Great Lakes Chemical Corporation, West Lafayette, Ind.

[ * ] Notice: The term of this patent shall not extend beyond the expiration date of Pat. No. 5,679,287.

[21] Appl. No.: 818,508

[22] Filed: Mar. 14, 1997

Related U.S. Application Data

[63] Continuation-in-part of Ser. No. 433,258, Apr. 28, 1995, Pat. No. 5,679,287.

[51] Int. Cl.$^6$ ............................. A23L 3/3445; F17C 1/00
[52] U.S. Cl. ..................... 252/399; 252/382; 252/384; 252/388; 252/605; 206/6; 422/10; 424/439; 426/394; 426/397
[58] Field of Search ..................................... 252/382, 384, 252/388, 605, 399, 380; 424/40, 439, 45; 426/394, 397, 316, 312, 318, 321, 654; 206/6; 422/9, 10, 40, 41; 514/1, 759; 96/148; 436/6, 8, 18, 321, 541, 544

[56] References Cited

U.S. PATENT DOCUMENTS

| | | | |
|---|---|---|---|
| 2,868,691 | 1/1959 | Porush et al. | 222/192 |
| 3,282,781 | 11/1966 | Macek et al. | 424/45 |
| 3,955,509 | 5/1976 | Carlson | 102/90 |
| 4,889,709 | 12/1989 | Mackles et al. | 424/45 |
| 4,971,716 | 11/1990 | Batt et al. | 422/34 |
| 4,997,664 | 3/1991 | Williams | 426/392 |
| 5,118,494 | 6/1992 | Schultz et al. | 424/45 |
| 5,124,053 | 6/1992 | Iikubo et al. | 252/8 |
| 5,230,884 | 7/1993 | Evans et al. | 424/45 |
| 5,292,499 | 3/1994 | Evans et al. | 424/45 |
| 5,314,682 | 5/1994 | Sweval et al. | 424/45 |
| 5,346,669 | 9/1994 | Sweval et al. | 422/34 |
| 5,374,434 | 12/1994 | Clapp et al. | 426/116 |
| 5,415,853 | 5/1995 | Hettche et al. | 424/45 |
| 5,443,861 | 8/1995 | Huhne | 427/249 |
| 5,453,445 | 9/1995 | Henry | 514/626 |
| 5,474,759 | 12/1995 | Fassberg et al. | 424/45 |
| 5,508,023 | 4/1996 | Byron et al. | 424/45 |
| 5,536,444 | 7/1996 | Hettche et al. | 252/305 |
| 5,615,742 | 4/1997 | Robin et al. | 169/45 |
| 5,635,161 | 6/1997 | Adjei et al. | 424/45 |

*Primary Examiner*—Benjamin Utech
*Assistant Examiner*—Deanna Baxam
*Attorney, Agent, or Firm*—Woodard, Emhardt, Naughton, Moriarty & McNett

[57] ABSTRACT

A method of improving the storage life of goods by storing the goods in an environment comprising heptafluoropropane at pressures of between about 0.1 atmospheres and about 2.0 atmospheres. Foods, pharmaceuticals, and other goods adversely affected by oxygen and/or moisture are effectively stored by the claimed method. The method is particularly effective for goods stored in plastic containers, and for goods stored in containers stoppered by rubber stoppers.

47 Claims, No Drawings

USES OF HEPTAFLUOROPROPANE

This application is a Continuation-In-Part of application Ser. No. 08/433,258 filed Apr. 28, 1995, now U.S. Pat. No. 5,679,287.

BACKGROUND OF THE INVENTION

1. Field of the Invention

The present invention relates to the containment of various products in a manner to protect the products from degradation and to reduce fire and explosion hazard. More particularly, the present invention relates to novel uses of heptafluoropropane for protecting products from oxygen and other degradation, and for protecting the products and the surroundings from a fire and/or explosion hazard.

2. Description of the Prior Art

Heptafluoropropane has been recently identified in the prior art as having several known uses which take advantage of certain characteristics of the compound. One notable property of heptafluoropropane is that it is not deleterious to the atmosphere ozone layer, in contrast to the chlorofluorocarbons.

Heptafluoropropane has been discovered to be non-flammable and has been found to be useful as a fire extinguishant, either alone or in combination with other extinguishants. Certain compositions for this use have been found to be azeotropic or near-azeotropic. The usefulness of heptafluoropropane in these regards has been disclosed in U.S. Pat. No. 5,124,053, issued to Iikubo on Jun. 30, 1992.

A study on the effectiveness of heptafluoropropane as an inerting compound has been reported in an article entitled Inerting of Propane-Air Mixtures with 1,1,1,2,3,3,3-Heptafluoropropane ($C_3F_7H$)—Nitrogen Blends, Zalosh et al., Chem. Phys. Processes Combust. 475–8 (1993). The study related to the use of heptafluoropropane in conjunctiong nitrogen gas to render propane-air mixtures inert.

Heptafluoropropane is also known to be useful as a propellant in certain applications. For example, Canada Pat. No. 2,086,492 describes the use of heptafluoropropane as a propellant with medical aerosol formulations. The heptafluoropropane is described as a suitable replacement for the environmentally unacceptable chlorofluorocarbon propellants. Further the heptafluoropropane is indicated to be useful at lower vapor pressures, to have better pressure-seal properties, elastomer compatibility and solvent power, and to provide higher formulation stability while being non-flammable. Propellant compositions including heptafluoropropane are also disclosed in Japan Patent No. 4,332,786 for use with skin drugs, antiperspirants, deodorants, etc.; European Patent 562032 for use with inhalation devices dispensing steroid or bronchodilator compositions; and PCT Application No. WO 9322415 A1 for use with cleaning compositions for electrical devices, mirrors, plastics, etc.

A non-flammable sterilant mixture containing ethylene oxide and heptafluoropropane is described in U.S. Pat. No. 5,314,682. The mixture is indicated to be non-flammable in all concentrations of air, and may further comprise nitrogen, carbon dioxide, argon of $CHF_3$ as a propellant. The composition is disclosed to be useful for sterilizing medical equipment and rubber and plastic goods, and as fumigants for furs, bedding and paper goods.

In U.S. Pat. No. 4,971,716 there is described the use of a composition of heptafluoropropane and ethylene oxide in sterilizing applications. The composition is noted as being chemically stable, minimally segregating, compatible with objects to be sterilized, improved as to suppression of flammability, and sufficient in terms of vapor pressure.

SUMMARY OF THE INVENTION

Briefly describing one aspect of the present invention, there is provided a method for storing atmosphere sensitive products which comprises surrounding the product with an amount of heptafluoropropane effective to reduce degradation of the product due to contact with oxygen and other deleterious gases in the air. In a particular method the product is provided in a container and the amount of heptafluoropropane used is sufficient to provide a protective blanket of heptafluoropropane above the product. In a related method, the container is closed and the heptafluoropropane constitutes at least about 5%, preferably at least about 20%, and as much as 100% v/v of the headspace in the container over the product.

Another aspect of the present invention comprises a method for containing atmosphere sensitive products, including foods, pharmaceuticals, chemicals and equipment, which comprises storing the product in a container with an amount of heptafluoropropane sufficient to reduce the risk of fire or explosion. For certain products, the heptafluoropropane serves both this purpose and that of protecting the product from degradation.

DESCRIPTION OF THE PREFERRED EMBODIMENT

For the purposes of promoting an understanding of the principles of the invention, reference will now be made to the following embodiments and specific language will be used to describe the same. It will nevertheless be understood that no limitation of the scope of the invention is thereby intended, such alterations and further modifications in the invention, and such further applications of the principles of the invention being contemplated as would normally occur to one skilled in the art to which the invention relates.

It has been determined that heptafluoropropane is useful in a variety of applications to protect/preserve food products, chemicals, etc. In addition, the presence of the heptafluoropropane provides an additional advantage or reducing or eliminating the risk of fire or explosion. The heptafluoropropane is provided in the headspace for the food or chemical product. That is, the heptafluoropropane is placed into the container, package, storage facility or the like and remains in the atmosphere above and surrounding the product to be protected. The heptafluoropropane is useful in connection with any product which is "atmosphere sensitive", which for purposes herein refers to the fact that the product will be contaminated, degraded, sensitized, spoiled, or physically or chemically altered as a result of exposure to oxygen or another component of a surrounding atmosphere. The heptafluoropropane works to replace or sufficiently modify the surrounding atmosphere to reduce or eliminate the deleterious effect which would otherwise occur due to exposure to the atmosphere.

The present invention utilizes heptafluoropropane in any of its isomeric forms. Heptafluoropropane is itself available commercially, and also may be conveniently produced via such routes as the reaction of commercially available hexafluoropropene with anhydrous HF as described in U.K. Patent 902,590. This compound has an ODP (oxygen deletion potential) of zero and therefore has no effect on stratospheric ozone.

The key to long term storage for many foods, pharmaceuticals, chemicals and equipment is the avoidance or reduction of oxygen contamination or degradation. It has been determined that heptafluoropropane is useful as a non-flammable adjunct in a variety of these situations. In particular, the heptafluoropropane is used to provide a desirable non-flammable and/or non-oxygen containing atmosphere.

Many products, particularly food, pharmaceutical and chemical products, are required to be packaged for protection against oxygen contamination and degradation. In addition, the products are frequently required to remain packaged for relatively long periods of time. It has been found that providing heptafluoropropane in the surrounding atmosphere for the contained products minimizes the potential for damage to the product and the surroundings. Also, storage of raw materials prior to processing benefits from the presence of heplafluoropropane by reducing contamination, minimizing reaction with oxygen, and reducing the likelihood of losses due to fire and explosion.

In some situations, the period of storage may be unusually long. By way of example, many products are specifically packaged or stored for long periods of time. Military packaging of supplies, including for example mechanical equipment and apparatuses and explosives, as well as foods, pharmaceuticals and other chemicals, is frequently directed to long term storage of many years. Packaging and storing these items in the presence of heptafluoropropane would protect the supplies from deterioration and would provide fire extinguishing or suppression protection. National disaster supplies in long term storage would similarly benefit from the presence of heptafluoropropane.

It is well known that food and related products must be properly packaged and stored to avoid degradation due to exposure to oxygen. In addition, in some situations the presence of oxygen can present severe fire and explosion threat. It has been found that heptafluoropropane is a safe and effective compound when used in conjunction with the storage and packaging of food and food products to minimize these problems. It is also noteworthy that heptafluoropropane has advantages over certain other inert storage gases, for example nitrogen, in that heptafluoropropane has a relatively high vapor density. As a result, the heptafluoropropane will tend to remain in a container even after the container is opened or develops a leak at the top. This is in contrast to nitrogen, which has essentially the same vapor density as air and may be easily lost from a container which has been opened or has developed a leak.

This concept also deals with providing an atmosphere where food, pharmaceuticals and other perishables are safe from bacterial or fungal attack. Furthermore, under an atmosphere of heptafluoropropane, decay and decomposition are also prevented since oxygen is eliminated by the heavier than air blanket that is provided.

In use with food and food products, the heptafluoropropane is placed in the surrounding atmosphere. Any manner effective to retain the heptafluoropropane in the proximity of the products is suitable. For example, in common situations the food items will be stored in cans, bottles or similar storage containers. The heptafluoropropane is simply added to the container to displace the air which would otherwise be present, and the container is then sealed. The amount of heptafluoropropane will vary with the application. In general, a sufficient amount of heptafluoropropane is added to at least provide a layer of the heptafluoropropane around and over the product. It will usually be convenient and preferable to simply fill essentially all of the container with heptafluoropropane. However, it may also be suitable to include only a portion of heptafluoropropane in the atmosphere surrounding the food product. In one aspect, the amount used is sufficient to provide a flame-suppressed atmosphere over the product, thereby minimizing the risk of fire or explosion, particularly in those situations where this would otherwise be a significant risk. Depending on the circumstances, at least about 5% v/v (volume of heptafluoropropane per volume of atmosphere), and more preferably at least about 20% of the atmosphere surrounding the food product is heptafluoropropane. Further desirable effects are achieved when using at least about 50% heptafluoropropane.

Related to the foregoing is the use of heptafluoropropane in connection with the storage of bulk food products, particularly grains, flours, etc. Examples of storage situations in which heptafluoropropane may be used would include grain silos and large storage containers, particularly closed receptacles, for storage of flour and the like. The heptafluoropropane is introduced into the storage facility for these products and maintained at the desired level. Introduction of the heptafluoropropane may occur as a one time addition, or may be periodic or continuous, depending on the circumstances. The method used is selected to maintain the desired amount of heptafluoropropane in the storage facility.

As indicated previously, the amount of heptafluoropropane provided is dependent on the nature of the product and the effect desired. In one aspect, a sufficient amount of heptafluoropropane is maintained in the atmosphere surrounding the bulk product to reduce fire and explosion hazards. In this regard, the heptafluoropropane is preferably maintained at a level of at least about 5% v/v, and more preferably at least about 20% v/v. In another aspect, the heptafluoropropane is utilized to reduce contact of the bulk food product with oxygen or other deleterious gases. According to one approach, an amount of heptafluoropropane is used which is sufficient to provide heptafluoropropane surrounding and overlying the bulk product. Another approach is to maintain an effective amount by volume percent to reduce degradation by oxygen, etc., which amount is preferably at least about 5% v/v, and more preferably at least about 20% v/v. Of course, even higher percentages of heptafluoropropane, for example at least about 50% v/v, will have the same or greater utility depending on the circumstances. Where practicable, such as in essentially closed storage facilities, and particularly where risk of degradation and/or fire/explosion is especially high, the heptafluoropropane is maintained as essentially 100% of the surrounding atmosphere within storage facility. Of course, the amount of heptafluoropropane used will be limited in those situations where the atmosphere must be breathable, in which case the amount of heptafluoropropane in the air is preferably less than about 9% v/v, and more preferably about 5%. This volume composition complies with the EPA Snap Rule, Federal Register Mar. 18, 1994, part II, volume 59, no. 53, page 13159, which defines a cardiotoxic No Observable Adverse Effect Level (NOEL) of greater than 9% v/v. Compositions may be used up to 99% v/v if exposure times are less than thirty seconds.

The preferred percentages of heptafluoropropane above perishables preferably are as high as possible to reduce or totally eliminate oxygen. The presence of high levels of heptafluoropropane works to inhibit the modes of oxygen or microbial spoilage that occur naturally in perishable items. Heptafluoropropane atmospheres by the same mode of action will eliminate insects from destroying perishables.

It has further been found that heptafluoropropane is useful in conjunction with the storage of chemicals, including pharmaceuticals, to protect against adverse effects due to the presence of oxygen or other gases in the air. Again, the heptafluoropropane is used to surround the chemicals to prevent degradation upon contact with gases, and/or to reduce fire and explosion potential. The use of heptafluoropropane is particularly well suited to chemicals stored in closed containers, especially where the storage will be maintained for extended periods of time.

The heptafluoropropane is used with chemicals to protect against degradation by in effect insulating the chemicals from the air. The heptafluoropropane is provided in an amount sufficient to surround the chemicals, i.e., by at least covering the chemicals and providing a protective layer over them. Therefore, the amount of heptafluoropropane used is that amount which will provide a covering layer over the chemicals. It will usually be preferred to fill the containers for such chemicals with essentially 100% heptafluoropropane. However, lesser amounts of heptafluoropropane may be used ranging preferably from at least about 5% v/v, and more preferably from at least about 20% v/v. Concentrations of at least about 50% will provide the same or additional advantages, particularly for products having greater potential for fire or explosion.

Because of the higher vapor density of heptafluoropropane, the use of heptafluoropropane has an advantage over other inert gases such as nitrogen. The vapor headspace above an oxygen-sensitive compound, for example requires only partial displacement of the surrounding air with heptafluoropropane to ensure complete protection from reaction with atmospheric oxygen. This is due to the heavier-than-air density of heptafluoropropane, which provides a gaseous "floating lid" which negates the need to completely displace all of the headspace air as required with nitrogen gas storage. In addition, the heavy density of heptafluoropropane will diminish or eliminate any diffusion of heptafluoropropane into the air headspace above a compound under storage, which again contributes to a very effective blanketing effect of heptafluoropropane.

It will be noted that the heptafluoropropane is useful in connection with chemicals which are dispensed from the bottom of a container. As a liquid chemical is dispensed from its container, air will enter in the headspace over the liquid. However, the heptafluoropropane will move down with the lowering liquid level, maintaining the protective blanket over the chemical and continuing to protect it from the air.

Protection from fire and/or explosion is also achieved by the use of heptafluoropropane with stored chemicals. Of course, many chemicals may present a hazard when contained in exposure to oxygen in the air. The presence of heptafluoropropane within the container is useful to provide a barrier between the chemical and the air to reduce this risk. Therefore, an amount of heptafluoropropane within the container is provided to at least provide a blanket of heptafluoropropane over the chemical. In a particular aspect, the heptafluoropropane is present in an amount of at least about 5% v/v of the air, and more preferably at least about 20% v/v. Depending on the nature of the contained chemical, the preferred amount of heptafluoropropane may be higher or lower, and for example may preferably be at least about 50% v/v.

In addition, the presence of heptafluoropropane may reduce the potential for fire and/or explosion upon opening or leakage of the chemical from a storage container. As the chemical is released from the container, the associated release of heptafluoropropane will suppress the possibility of a fire or explosion in the immediate vicinity until the chemical is more dispersed.

Heptafluoropropane could be added, for example, to the headspace to provide protection against oxygen degradation, fire and potential explosions originating in the headspace of large fuel storage tanks and vessels. This would apply, for example, to the U.S. Strategic Petroleum Reserve system (600 million barrels in 1995), as well as world-wide storage facilities. This would also apply to any fuel or gasoline storage vessels at refineries, distribution terminals, and industrial plants. In the case of local and small scale storage tanks such as those present in gasoline refueling stations, heptafluoropropane could be added to the headspace of underground storage tanks to provide fire and explosion protection as described. In the case where fuel has already ignited and is burning on the surface of a storage tank or vessel, heptafluoropropane could be introduced at a subsurface level in such quantity as to have it migrate to the surface of the flammable liquid and thereby break the interface and contact of oxygen with the flammable liquid and subsequently extinguish the flame.

The present invention also contemplates the use of blends of heptafluoropropane with other gases where applicable. In those instances in which the heptafluoropropane is used to reduce fire or explosion hazard, it is suitable to blend the heptafluoropropane with other inert gases or with fire extinguishants compatible with the application. For situations in which the heptafluoropropane is used to reduce degradation due to atmospheric oxygen or other gases, then it is contemplated that the heptafluoropropane may be blended with other inert gases. For example, if oxygen degradation is the concern, then it may be suitable to blend the heptafluoropropane with nitrogen for the purpose of reducing cost or for other indicated reasons. In such instances, it may be desirable to maintain the heptafluoropropane at a level which provides other advantageous effects, such as the reduction of fire or explosion potentials where existent.

EXAMPLE 1

Heptafluoropropane is injected into the headspace of a food product container. The food product is one which readily identified as atmosphere sensitive, for example dairy products, breads and most all other canned or otherwise packaged foods. Providing about 5% heptafluoropropane in the atmosphere surrounding the contained food product reduces the degradation of the food product. Similar testing with 20%, 50% and 100% heptafluoropropane also reduces degradation of the food product, generally with correspondingly increasing effect.

EXAMPLE 2

Pharmaceutical products which are atmosphere sensitive, including various tablet and capsule preparations and parenterals are protected by being surrounded with an atmosphere containing at least a portion of heptafluoropropane. The addition of levels of heptafluoropropane at 5%, 20%, 50% and 100% v/v in the headspace over the contained pharmaceuticals reduces the deleterious effects of oxygen and other components of normal atmosphere, thereby increasing the integrity of the product and extending its shelf life.

EXAMPLE 3

Similar tests for various atmosphere sensitive chemicals yield similar results. Heptafluoropropane is injected into the headspace of the chemical container to provide a protective gaseous floating lid. The presence of heptafluoropropane at the indicated levels of 5%, 20%, 50% and 100% provides generally increasing efficacy in protecting the chemicals from degradation.

EXAMPLE 4

The use of heptafluoropropane for the cited purposes is also demonstrated for bulk stored products, including foods, pharmaceuticals and other chemicals, including fuels and commercial explosives and explosive materials and pyrophoric materials, and packaging of said materials. Results similar to those cited in Examples 1–3 are achieved. In particular, protection from the atmosphere is obtained while the use of levels 5% and 9% heptafluoropropane provide atmospheres which are breathable.

EXAMPLE 5

The use of heptafluoropropane for the cited purposes is also demonstrated for bulk stored products, including mechanical equipment and apparatuses, electrical and electronic equipment, and military packaging of said equipment. Results similar to those cited in Examples 1–4 are achieved. In particular, protection from the atmosphere is obtained while the use of levels 5% and 9% heptafluoropropane provide atmospheres which are breathable.

EXAMPLE 6

In utilization of heptafluoropropane to protect oxygen-sensitive materials, additional features were discovered that clearly demonstrate a superior advantage of this compound over other gases used as inerting agents. For example, two aqueous solutions of oxygen-sensitive photographic developers were placed in glass bottles and filled to 90% of the bottle's capacity, thereby leaving a 10% headspace of air. The headspace atmosphere of the first bottle was left undisturbed. The air in the headspace of the second bottle was replaced with an atmosphere of essentially 100% pure heptafluoropropane.

Each bottle was tightly closed with a screw-top lid that is impervious to gas flow or exchange. The bottles then remained in storage and undisturbed for over two weeks. After storage, each bottle was opened for removal of some of the liquid. The bottle containing air headspace exhibited a "hissing" sound as a new supply of air rushed into the bottle to replace the approximately 20% volume of oxygen that was consumed by photographic developer. However, opening of the bottle containing heptafluoropropane exhibited no such effect as no apparent chemical reaction had occurred between the headspace gas and the photographic developer.

These observations of storing oxygen-sensitive compounds under atmospheres of heptafluoropropane clearly demonstrated two important advantages of heptafluoropropane. One, heptafluoropropane (as compared to oxygen) did not react with the photographic developer and did not reduce or diminish its chemical activity. Second, the headspace of heptafluoropropane (as compared to air/oxygen) was not reduced in pressure, thereby preventing an inrush of air as the bottle was opened. Thus, introduction of new supply of air and destructive oxygen did not occur in the bottle containing a headspace of heptafluoropropane.

EXAMPLE 7

Additionally, heptafluoropropane is superior to other heavier-than-air compounds such as carbon dioxide which will eventually dissolve in water and form an aqueous solution of carbonic acid. Due to the alkaline nature of most photographic developers, any formation of carbonic acid would be quite detrimental in reducing the functionality of the developer. Heptafluoropropane is also superior to nitrogen gas as it provides a very dense blanket of protection against introduction of oxygen.

EXAMPLE 8

The effect of heptafluoropropane on the growth of fungal strain 86 (white colored spores) was tested. A 5 microliter drop of fungal spores was inoculated to the centers of petri dishes containing potato dextrose agar medium or coconut agar medium. The culture plates (3 reps of the PDA plates and 2 reps of the coconut plates) were placed in dessicators containing air or heptafluoropropane with approximately 5% air. After 7 days incubation at 29° C., colony diameter, spore production and aflatoxin were determined. Spore counts were determined by washing plates with 5 ml of water and counting spores using a hemacytometer. Aflatoxin can be visualized as a blue fluorescence under UV irradiation around the fungal colonies grown on coconut agar medium. Aflatoxin was determined by extracting plates with acetone and analyzing the acetone extracts on thin layer chromatography. Aflatoxin was estimated by comparisons with known standard concentrations of Aflatoxin B1.

Results

The most strikging effect of the heptafluoropropane treatment was a asporulation. There were essentially no spores produced on the plates of the heptafluoropropane treated cultures. There was also about 20 to 50% inhibition of growth as measured by colony diameter. Aflatoxin did not appear to be inhibited when the plates were viewed under UV irradiation. Later analysis of one of the plates confirmed these findings. For the PDA plates, the colony diameter (average of 3 plates) for the air (control) plate was 50 mm and the spore production (average of 2 plates) was $1.55\times10^8$. The heptafluoropropane plate had a colony diameter of 39 mm and no spores. For the coconut agar plates, the air (control) plate had a colony diameter (one plate) of 65 mm and aflatoxin was measured at 400 micrograms/plate. The heptafluoropropane plate had a colony diameter (one plate) of 30 mm and the aflatoxin was measured at 400 micrograms/plate.

EXAMPLE 9

The purpose of this example was to repeat the test done in Example 8 and to test the effects of heptafluoropropane on the growth and aflatoxin production on corn kernels. A nitrogen atmosphere was added as an additional treatment. As in Example 8, a vacuum was drawn on the dessicators, which were then filled with air, heptafluoropropane, or nitrogen. This process was done 4 times to assure the greatest displacement of gas in the dessicator as possible. The following treatments were placed in the test atmospheres:

1. Corn kernels were conditioned for two days at 5° C. to raise the moisture to about 18 percent. Fifty kernels were wounded with an 18 gauge needle at the position of the embryo and inoculated with fungal strain NRRL 3357 (wild-type), submerging the kernels in a spore suspension of $1.7\times10^6$ spore/ml. Fifty unwounded kernels were also inoculated with the same spore suspension. Fifty kernels were selected and not inoculated.
2. A 5 microliter drop of fungal spores was inoculated to the centers of petri dishes containing coconut agar medium.

After 6 days of incubation at 29° C., colony diameter, spore production and aflatoxin were determined. The colony diameters on coconut were measured and the spores were washed from the plates as in Example 8. The plates were then extracted with acetone and analyzed for aflatoxin as in Example 8. The kernels were analyzed by first washing the spores off the 50 kernel samples with 5 ml of water and counting the spores as in Example 8. Two subsamples of 10 kernels were taken from each of the 50 kernel samples (after the spore washing procedure). These subsamples were ground in a mortar and extracted with acetone. The extracts were analyzed on TLC as in Example 8.

Results

After 6 days of incubation, sporulation was clearly visible from the wounded/inoculated kernels in the air atmosphere. No sporulation was visible in the heptafluoropropane or the nitrogen atmospheres. Growth inhibition (80%) was observed in the heptafluoropropane and nitrogen atmospheres as compared to the air atmosphere. Aflatoxin was detected only in the wounded/inoculated kernels and the coconut agar plates in the air atmosphere. For the coconut plates (average of 2 plates), the air plate had a colony diameter of 85 mm, a spore production of $1.2\times10^9$ and aflatoxin of 200 micrograms. The nitrogen plate had a colony diameter of 10 mm and no spore production of aflatoxin. The heptafluoropropane plate had a colony diameter of 18 mm, no spore production and aflatoxin of at most a trace. For the kernels, the air treatment yielded spore production for the wounded/inoculated of $2.7\times10^8$, for the not wounded/inoculate of $1.0\times10^{8,}$ and for the not wounded/not inoculated of $2.5\times10^7$. For the nitrogen treated kernels, the spore production for the wounded/inoculated was $1\times10^5$, for the not wounded/inoculated was $2\times10^6$, and for the not wounded/not inoculated was none. For the heptafluoropropane treated kernels the spore production for the wounded/inoculated was $1.2\times10^6$, for the not wounded/inoculated was $1.2\times10^7$, and for the not wounded/not inoculated was none.

EXAMPLE 10

This example tested one inoculated (strain NRRL 3357) coconut agar plate in either air or heptafluoropropane. The amount of oxygen in the chamber was determined at the beginning of the example. The example was stopped after 7 days incubation. Results were similar to those of Example 9. Growth, sporulation and aflatoxin production were inhibited in the heptafluoropropane atmosphere.

While the invention has been illustrated and described in detail in the foregoing description, the same is to be considered as illustrative and not restrictive in character, it being understood that only the preferred embodiments have been shown and described and that all changes and modifications that come within the spirit of the invention are desired to be protected.

In a further aspect of the invention heptafluoropropane ("HFP") is used to provide an atmosphere suitable for storing foods and medications at pressures of between about 0.1 atmospheres and about 2.0 atmospheres, preferably about 0.75 to about 1.25 atmospheres, and most preferably about 1.0 atmospheres.

In certain preferred embodiments, the storage life of goods, including foods and/or pharmaceuticals, is increased by storing those goods in plastic containers substantially filled with heptafluoropropane at about 0.1 to about 2.0 atmospheres, preferably 0.75 to 1.25 atmospheres, and most preferably about atmospheric pressure. It is known to the art that the plastic barriers currently used to store goods such as pharmaceuticals and foods do not totally inhibit the infusion of oxygen into the package. Although the storage packages are commonly filled with an inert gas to lengthen the storage life of the goods, the gases used by the prior art (particularly, nitrogen and carbon dioxide) do not prevent the infusion of oxygen or moisture into the packaging. Thus, oxygen and moisture slowly leak into the packaging and the storage life of the goods contained therein is deleteriously affected.

It has now been surprisingly found that introducing heptafluoropropane into a plastic storage container to have the indicated pressure inhibits the infusion of oxygen, moisture, and other contaminants across the plastic barriers. Because heptafluoropropane is heavier than air, even modest amounts of HFP can be used to provide a protective barrier around the goods. Preferably though, the storage container is substantially filled with HFP.

It is further known to the art that rubber compounds are commonly used as stoppers in containers containing, for example, pharmaceuticals. Unfortunately, the rubber compounds presently used by the art contain certain additives that can adversely affect the safety, efficacy or storage life of the goods stored in the container. Thus, rubber compounds used for stoppers must be tested before they can be used in injectable containers. Even then, additives find their way out of the rubber and into the injectable medication, resulting in a shortened life of the packaged product.

Accordingly, in a further aspect of the invention heptafluoropropane is used to provide a barrier between a rubber stopper and a stored good to inhibit the rate of movement of additives from the rubber stopper to the good, particularly when the good is an injectable solution.

In one preferred embodiment, a storage container containing goods to be stored is first evacuated and is then substantially filled with heptafluoropropane. The process may be repeated as necessary to ensure that all oxygen has been removed. After the concentration of HFP reaches the desired pressure, the container is sealed off. Since HFP is an expanding gas, it will cool upon loading the container. It will therefore warm as it reaches room temperature, and could, in a closed vessel, cause increased pressure. Hence, some allowance should be made for the increase in pressure that occurs with an increase in temperature upon loading any sealed vessel. This is particularly applicable in manufacturing processes where food or pharmaceuticals are stored in containers protected with HFP. The HFP is preferably added in the amounts required to provide the previously indicated pressures ranging preferably from about 0.1 to about 2.0, and most preferably about atmospheric pressure, at room temperature.

A preferred manufacturing process involves adding HFP directly to containers or loading containers in a pure atmosphere of HFP. In one preferred embodiment, heptafluoropropane is used to totally eliminate oxygen and reduce moisture. Effective packaging occurs when sufficient HFP has been loaded to prevent the infusion of oxygen through packaging barriers, and the emission of HFP to outside the barriers.

It is to be appreciated that HFP can be readily added in the manufacturing process to provide the following benefits:

1. Inhibition of microorganism growth through oxygen deprivation.
2. Inhibition of oxygen reaction with product contents.
3. Elimination of corrosion through reaction of moisture and oxygen.
4. Elimination of decomposition and degradation of products due to adverse atmospheric conditions.
5. Extended shelf life for food and pharmaceuticals.

6. Extended shelf life for any perishable items affected by oxygen and moisture.

The present invention has application to a wide variety of materials which are stored in a closed environment, whether in bulk storage facilities such as silos, warehouses or rooms, or in smaller packages or containers used for individual or groups of items. Further examples of product packagings that benefit from the use of HFP at the indicated levels of about 0.1 to about 2.0 atmospheres, preferably about 0.75 to about 1.25 atmospheres, and most preferably about 1.0 atmosphere, include:

1. Pharmaceuticals—including injectables, pills, tablets, and other forms of liquid or solid pharmaceutical items that could be preserved under an atmosphere of HFP;
2. Foods—including human and animal foods of all varieties, both solids and liquids, including but not limited to feed grains stored in silos or other bulk storage facilities. Storage under an atmosphere of HFP inhibits the growth of microorganisms and inhibits the decomposition of food products. Foods such as cereals and other perishable items could be packaged such that HFP resides in the package until opened; and
3. Items adversely affected by atmospheric gases, primarily oxygen, moisture and/or corrosion. Such items include all of the previously identified items such as liquid or solid chemicals, electrical and mechanical components and devices, and hazardous materials such as explosives, fuels, and other flammable compounds. The invention is useful with relatively short term storage, since even limited time periods can result in adverse consequences for the item. Even further advantage may be found for long term storage, such as frequently found for military items and items for emergency stock piling.

It is also to be appreciated that a wide variety of containers may be used in the present invention, including plastic bags with sealable tops that would be sealed during the manufacturing process after loading. Such bags would be sealed in a fashion to prevent the escape of HFP or the infusion of oxygen. In addition, even larger bulk facilities benefit from the invention provided that the facility is sufficiently closed to retain the HFP in the quantity/pressure indicated.

Filling of containers may involve evacuation as described above, but it could also involve the flushing and recapture of HFP. For example, a continuous stream of HFP passing through a vessel would eliminate the presence of oxygen after a certain period of time. The HFP oxygen mixture could then be recycled by capturing the HFP and eliminating the oxygen.

An alternative method of use comprises a method similar in some respects to what is currently practiced in the vegetable industry using carbon dioxide. Carbon dioxide, being heavier than air (although not as heavy as HFP), is provided to a lower level packaging area. The lower level packaging area, containing only an atmosphere of carbon dioxide and products to be packaged, are lowered into a sublevel thereby forcing out any oxygen. HFP could be used in a similar fashion. The total atmosphere in this manner eliminates oxygen and the entire packaging process is carried out in an atmosphere of HFP. This method ensures the proper pressure and avoids the expansion of gases upon heating since loading would occur with expanded gases at atmospheric pressure.

It is further to be appreciated that in none of these cases is the container containing HFP considered to be a "pressured system," although some changes in internal pressure can occur due to changes in ambient temperature. As previously indicated, ambient (i.e., atmospheric) pressures are most preferred, although pressures of between about 0.5 atmospheres to about 2.0 atmospheres have been shown to be effective in some preferred embodiments.

Reference will now be made to specific examples using the processes described above. It is to be understood that the examples are provided to more completely describe preferred embodiments, and that no limitation to the scope of the invention is intended thereby.

EXAMPLE 11

Vegetables are stored in plastic containers substantially filled with heptafluoropropane at a pressure of 0.5 atmospheres. The storage life of the vegetables is extended from two to three days to two to three weeks by storing under an HFP atmosphere.

EXAMPLE 12

Packaging for military and emergency purposes is improved by storing the goods in an HFP environment. In particular, military retort pouches (pouches where the food is actually cooked in the container) are filled with HFP at a pressure of about 2.0 atmospheres, and the food is sealed in. The storage life of the pouch is thereby improved.

EXAMPLE 13

Pharmaceutical products are provided in containers which are enclosed by a rubber stopper and a rubber septum, and HFP is added at atmospheric pressure. The storage life of the pharmaceuticals is thereby improved.

EXAMPLE 14

A wide variety of items are contained in substantially closed containers or storage facilities which maintain the HFP at pressures of 0.1 to 2.0 atmospheres, including 0.75, 1.0 and 1.25 atmospheres. Reduced adverse effect on the items due to contact with atmospheric gases and moisture is realized.

While the invention has been illustrated and described in detail in the drawing and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of storing goods comprising:
    storing the goods in a closed container containing the goods and a surrounding gaseous space, the gaseous space including a gas at about atmospheric pressure and comprising heptafluoropropane.
2. The method of claim 1 wherein the gas consists essentially of heptafluoropropane.
3. The method of claim 1 wherein said goods are pharmaceuticals.
4. The method of claim 1 wherein said goods are foods.
5. The method of claim 1 wherein said goods are affected by corrosion.
6. The method of claim 1 wherein said goods are adversely stored in a container enclosed by a rubber septum or stopper.
7. The method of claim 1 wherein said storing is in a container made of a plastic which does not prevent the infusion of oxygen across the plastic container barrier.

8. The method of claim 1 in which the goods are physically or chemically altered by exposure to the atmosphere.

9. The method of claim 1 in which the goods are not fuels or explosives.

10. The method of claim 1 in which the gas comprises at least about 5% v/v heptafluoropropane.

11. The method of claim 1 in which the gas comprises at least about 20% v/v heptafluoropropane.

12. The method of claim 1 in which the gas comprises at least about 50% v/v heptafluoropropane.

13. The method of claim 1 in which the gas comprises an amount of heptafluoropropane sufficient to form a layer around and over the goods.

14. The method of claim 1 in which the gas consists essentially of heptafluoropropane and at least one other inert gas.

15. The method of claim 1 in which the gas consists essentially of heptafluoropropane and air.

16. A method of storing goods comprising:
   storing the goods in an environment consisting essentially of heptafluoropropane, said heptafluoropropane being provided at a pressure of between about 0.1 atmospheres and about 2.0 atmospheres.

17. The method of claim 16 in which said heptafluoropropane is provided at a pressure of between about 0.75 and about 1.25 atmospheres.

18. The method of claim 16 in which said heptafluoropropane is provided at a pressure of at most about one atmosphere.

19. The method of claim 16 in which the environment consists of heptafluoropropane.

20. The method of claim 16 in which the environment further comprises at least one other inert gas.

21. The method of claim 16 in which the environment further comprises air.

22. A method of storing goods comprising:
   storing the goods in a container made of a plastic which does not prevent the infusion of oxygen across the plastic container barrier, the container including an environment comprising heptafluoropropane, said heptafluoropropane being provided at a pressure of between about 0.1 atmospheres and about 2.0 atmospheres.

23. The method of claim 22 in which said heptafluoropropane is provided at a pressure of between about 0.75 and about 1.25 atmospheres.

24. The method of claim 22 in which said heptafluoropropane is provided at a pressure of at most about one atmosphere.

25. The method of claim 22 in which the environment consists of heptafluoropropane.

26. The method of claim 22 in which the environment further comprises at least one other inert gas.

27. The method of claim 22 in which the environment further comprises air.

28. A method of storing foods comprising:
   storing the foods in an environment comprising heptafluoropropane, said heptafluoropropane being provided at a pressure of between about 0.1 atmospheres and about 2.0 atmospheres.

29. The method of claim 28 in which said heptafluoropropane is provided at a pressure of between about 0.75 and about 1.25 atmospheres.

30. The method of claim 28 in which said heptafluoropropane is provided at a pressure of at most about one atmosphere.

31. The method of claim 29 in which the environment further comprises at least one other inert gas.

32. The method of claim 29 in which the environment further comprises air.

33. The method of claim 29 in which the environment consists essentially of heptafluoropropane.

34. The method of claim 33 in which the environment consists of heptafluoropropane.

35. The method of claim 29 in which the gas comprises at least about 5% v/v heptafluoropropane.

36. The method of claim 35 in which the gas comprises at least about 20% v/v heptafluoropropane.

37. The method of claim 36 in which the gas comprises at least about 50% v/v heptafluoropropane.

38. The method of claim 29 in which the gas comprises an amount of heptafluoropropane sufficient to form a layer around and over the foods.

39. A method of storing goods in a closeable container comprising:
   a) placing the goods into the closeable container;
   b) placing a gas consisting essentially of heptafluoropropane into the container, the heptafluoropropane being provided at a pressure of between about 0.1 atmospheres and about 2.0 atmospheres; and
   c) closing the container to retain the heptafluoropropane and the goods therein.

40. The method of claim 39 in which said placing of the goods is performed prior to said placing of the gas consisting essentially of heptafluoropropane.

41. The method of claim 40 in which said placing of the goods is into a container initially containing air, and said placing of the gas consisting essentially of heptafluoropropane includes replacing at least some of the air in the container with the heptafluoropropane.

42. The method of claim 41 in which said placing of the gas consisting essentially of heptafluoropropane comprises placing a sufficient amount of the heptafluoropropane into the container to have at least about 5% v/v heptafluoropropane in the container at the time of closing the container.

43. The method of claim 42 in which said placing of the gas consisting essentially of heptafluoropropane comprises placing a sufficient amount of the heptafluoropropane into the container to have at least about 20% v/v heptafluoropropane in the container at the time of closing the container.

44. The method of claim 43 in which said placing of the gas consisting essentially of heptafluoropropane comprises placing a sufficient amount of the heptafluoropropane into the container to have at least about 50% v/v heptafluoropropane in the container at the time of closing the container.

45. The method of claim 41 in which said placing of the gas consisting essentially of heptafluoropropane comprises placing a sufficient amount of the heptafluoropropane into the container to have about 100% v/v heptafluoropropane in the container at the time of closing the container.

46. The method of claim 39 in which said placing of the gas includes providing the heptafluoropropane at a pressure of between about 0.75 and about 1.25 atmospheres.

47. The method of claim 39 in which said placing of the gas includes providing the heptarluoropropane at a pressure of at most about one atmosphere.

* * * * *